United States Patent [19]
Hamlin et al.

[11] Patent Number: 5,408,992
[45] Date of Patent: Apr. 25, 1995

[54] ENDOSCOPIC DEVICE FOR INTRAORAL USE

[75] Inventors: David Hamlin, Langhorne, Pa.; Arthur C. McKinley, Bradford, Mass.; William Habermann, Blairstown, N.J.

[73] Assignee: British Technology Group USA Inc., Gulph Mills, Pa.

[21] Appl. No.: 148,097

[22] Filed: Nov. 5, 1993

[51] Int. Cl.⁶ .................................................. A01B 1/00
[52] U.S. Cl. ........................................ 128/4; 128/6; 128/7
[58] Field of Search ...................... 128/4, 6, 7; 433/29

[56] References Cited

U.S. PATENT DOCUMENTS

| | | | |
|---|---|---|---|
| 4,173,392 | 11/1979 | Ekinaka et al. | |
| 4,211,229 | 7/1980 | Wurster | |
| 4,354,734 | 10/1982 | Nakahashi | |
| 4,390,012 | 6/1983 | Mizumoto | 128/4 |
| 4,561,446 | 12/1985 | Hetz | 128/7 X |
| 4,615,333 | 10/1986 | Taguchi | |
| 4,656,999 | 4/1987 | Gtorz | |
| 4,802,461 | 2/1989 | Cho | 128/7 |
| 4,850,342 | 7/1989 | Hashiguchi et al. | 128/6 |
| 4,863,304 | 9/1989 | Bauer et al. | 128/4 |
| 4,878,485 | 11/1989 | Adair | 128/4 X |
| 4,942,867 | 7/1990 | Takahashi | |
| 4,974,580 | 12/1990 | Anapliotis | 128/4 |
| 5,124,797 | 6/1992 | Williams et al. | |
| 5,179,620 | 1/1993 | Hosaka et al. | |
| 5,188,092 | 2/1993 | White | 128/6 X |
| 5,207,213 | 5/1993 | Auhll et al. | 128/6 |
| 5,237,984 | 8/1993 | Williams, III et al. | 128/4 |

OTHER PUBLICATIONS

Dental Products Report, Dec., 1992, pp. 58–59.

*Primary Examiner*—Richard J. Apley
*Assistant Examiner*—Beverly A. Meindl
*Attorney, Agent, or Firm*—Joel F. Spivak

[57] ABSTRACT

An inta-oral device for viewing the oral cavity comprises a handle having a tube extending therefrom for insertion into the oral cavity to be viewed; an optical system within the tube; a video camera within the handle and illuminating means for illuminating the cavity; and a removable, rigid, sterilizable sheath completely enclosing the tube and illuminating means to prevent their exposure to the oral cavity. The optical means provides a non-reversed image to appear on a video screen.

12 Claims, 3 Drawing Sheets

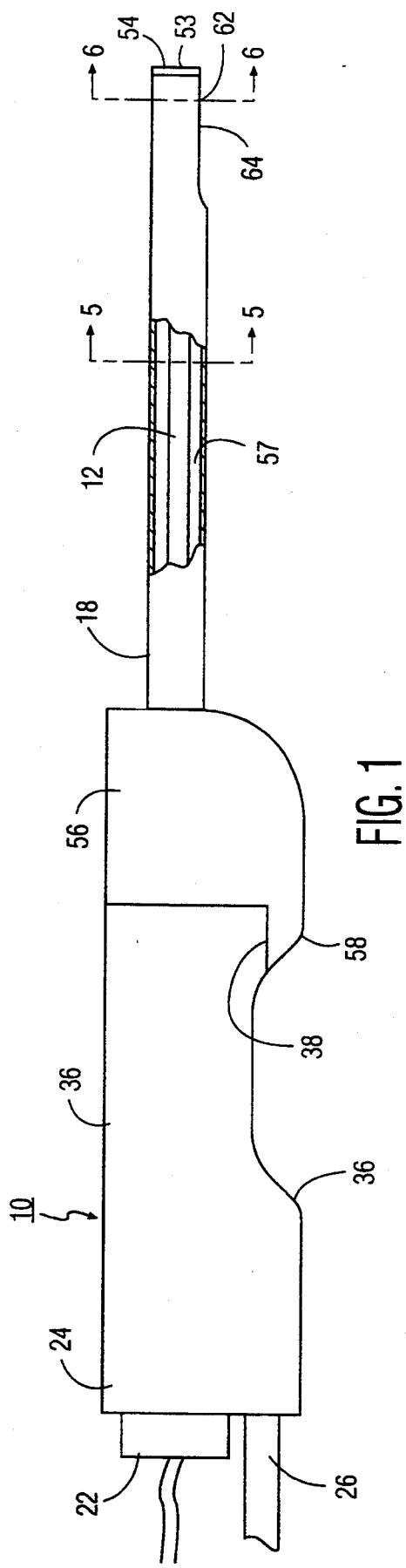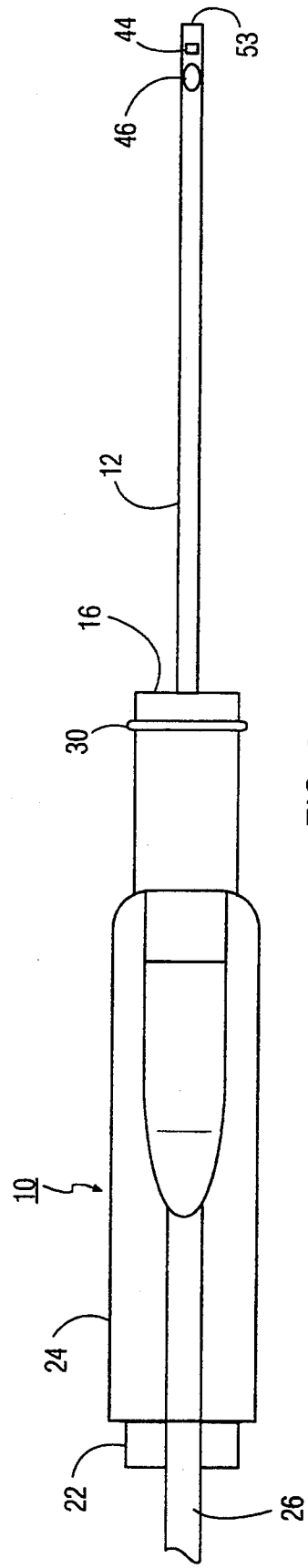

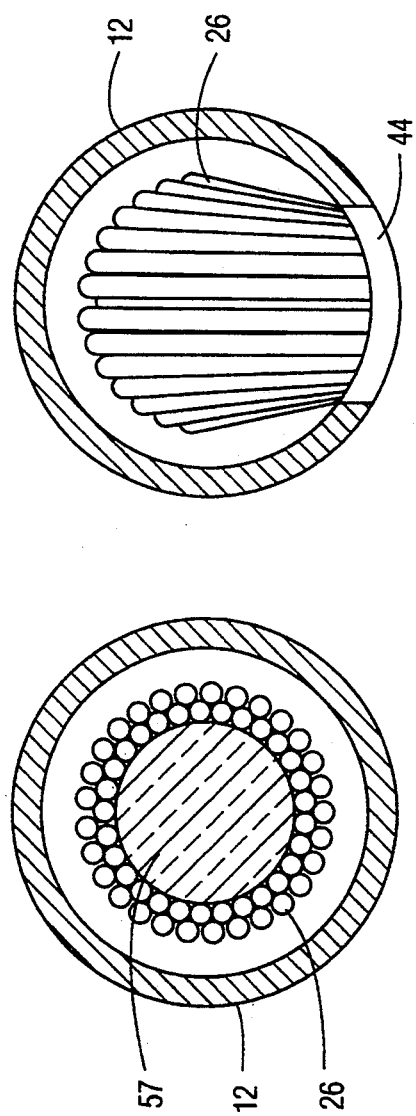
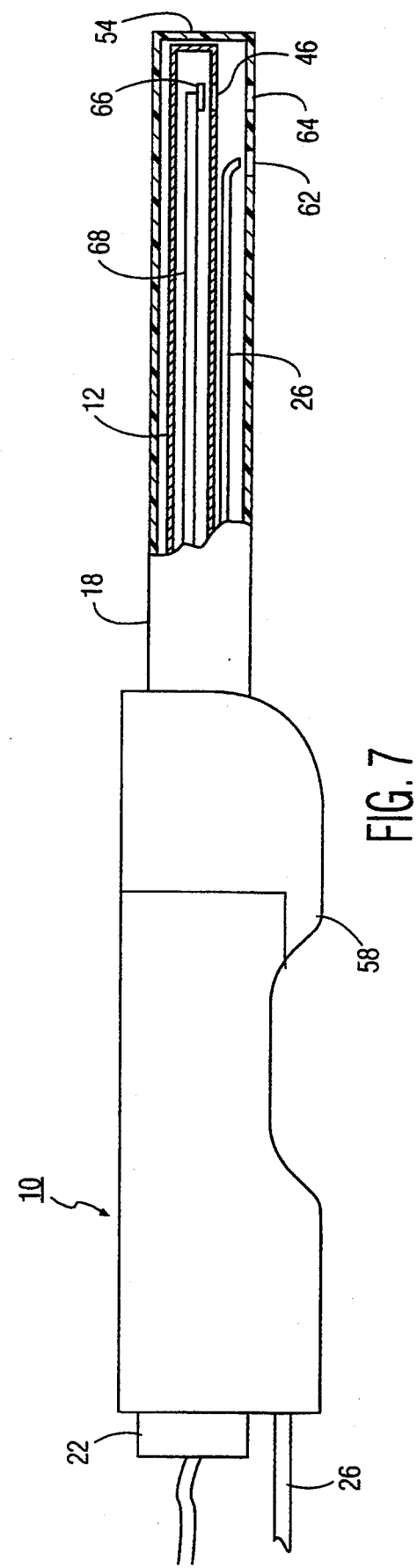

ENDOSCOPIC DEVICE FOR INTRAORAL USE

FIELD OF THE INVENTION

This invention relates to an imaging system and particularly to an autoclavable intraoral endoscopic or bore-scope type of device for viewing ones mouth via a video screen. More particularly, the preferred embodiment provides an autoclavable intraoral imaging system which includes an autoclavable sheath and a handpiece adapter for use in such a system.

BACKGROUND OF THE INVENTION

Bore-scopes, endoscopes and similar devices for viewing internal body structures and cavities on a video screen utilizing an imaging device and a video camera are well known. Such devices have been used widely in the medical field for viewing internal human tissue and in industry for inspecting the hidden surfaces of various structures.

A typical endoscopic system comprises an endoscopic lens device, a video camera and a video display and/or storage media. The endoscopic device comprises a supporting member, having a forward end to which there is attached an endoscopic tube which enters the internal cavity to be viewed. The endoscopic tube in some cases, but not all (some systems rely on ambient lighting), contains a light guide connected to a light source, e.g. a fiber optic bundle for illuminating the surfaces within the cavity and a lens system for conveying light reflected from these surfaces back to the video camera. The video camera is generally mounted on the supporting member opposite the endoscopic tube. Low level electrical signals developed by the camera (e.g. a CCD Chip) are conveyed through appropriate wires to a signal processing device for creating a video display and/or recording a video image. In some smaller endoscopic systems (e.g. intraoral devices), the endoscopic tube is directly coupled to an SCR camera without an intervening support member.

For infection control, one recent requirement for such devices is that any portion of the device which enters a body cavity must be either discarded or sterilized before reuse. Generally, in previous apparatus, e.g. the intraoral camera system marketed by AcuCam of Canoga Park, Calif., the entire forward end of the endoscopic device, including the light guide and lens system, is detached from the camera for sterilization. Since sterilization, e.g. by autoclaving, is generally time consuming, the dentist would require several expensive lens-fiber optic system members to be on hand for use with subsequent patients. Further, repeated sterilization can degrade or damage the optics and light guides. Hence, a need exists for a device which would allow immediate reuse of a lens-fiber optic system member without delay, damage, or inventory expense associated with the necessity of sterilization.

Another shortcoming of the aforementioned intraoral system is that the same member which is inserted into the oral cavity is held by the user. While the user (dentist) generally wears protective gloves and the portion held is generally a short distance from the inserted portion of the device, it would still be safer for both the user and the patient, that the user should not have to hold that portion of the device at all while in use. Any surface not being exposed directly, either external or internal to the patient's body cavity is considered an environmental surface and is/can be treated by appropriate high level disinfection rather than by sterilization.

A further disadvantage of prior art devices is that the image on the screen is the mirror image of the actual field being observed and movement to the left in the oral cavity appears as movement to the right on the screen. This often leads to a difficulty in manipulation of the device. It is therefore desirable that the screen and actual motion of the device appear identical.

Still another disadvantage occurring with respect to the prior art intraoral system is that the bulkiness or size of the inserted portion tends to block the vision of the user with respect to the oral cavity and the patient may tend to gag.

Yet another disadvantage of some intraoral systems is that the optical system is not sealed from the oral (or other) cavity thereby requiring sterilization of that member containing that system after each use. Such shortcomings are difficult or impossible to address without potential fatal damage to precision electronics and optics.

The novel device substantially eliminates the above problems.

SUMMARY OF THE INVENTION

An intraoral device for viewing a field within the oral cavity comprising a handle having a size and shape to allow the user to easily and comfortably hold and manipulate the device without touching any portion thereof which is insertable into the oral cavity; means associated with said handle for detachably and/or interchangeably mounting a video camera therein; a rigid optics tube mounted to said handle, said optics tube being closed at its distal end; illuminating means for illuminating the field to be viewed; optical means contained within the rigid optics tube for transmitting and focussing light reflected from the illuminated field onto the plane of the video camera; a rigid removable sterilizable sheath secured by the handle and overlying both said optics tube and said illuminating means and completely isolating them from contact with the field or walls of the oral cavity; and means for allowing light to pass from said illuminating means out of said sheath and means for allowing light reflected from the field to pass through said sheath and optics tube and int said optical means, said light from said illuminating means and said light entering said optical means being essentially perpendicular to the axis of the optics tube; and said optical means including a roof prism for image inversion.

BRIEF DESCRIPTION OF THE DRAWINGS

FIG. 1 is a side, partially cut-away, elevational view of a preferred embodiment of the assembled device.

FIG. 2 is a bottom elevational view of the device of FIG. 1 without the sheath.

FIG. 5 is a front cross-sectional view of the optics tube of the device of FIG. 1 along section 5—5.

FIG. 6 is a front cross-sectional view of the optics tube of the device of FIG. 1 along section 6—6.

FIG. 7 is a side, partially cross-sectional view, of another embodiment of the device.

DETAILED DESCRIPTION OF THE INVENTION

Figure 3:
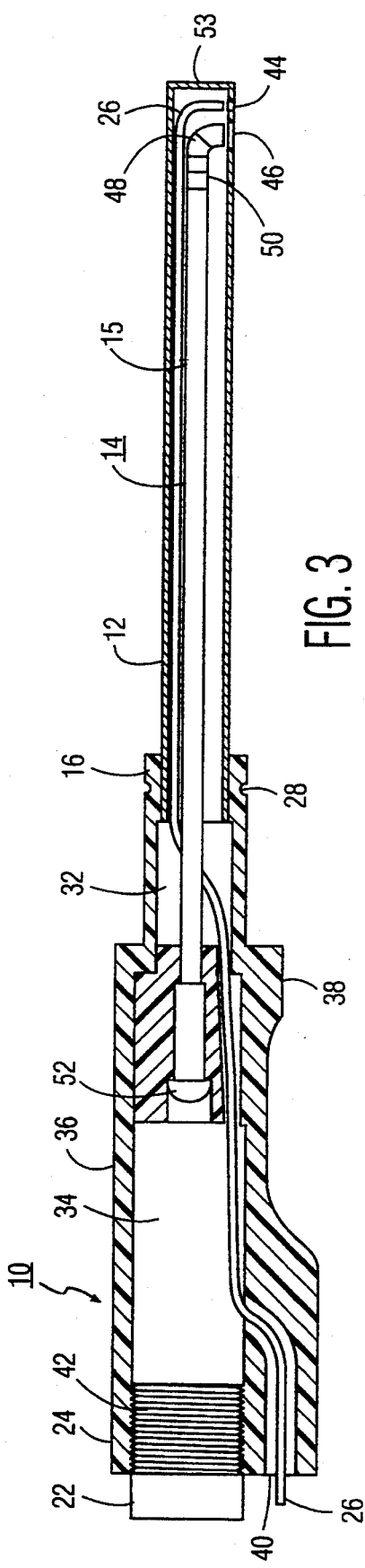
FIG. 3 is a side cross-sectional view of the device of FIG. 1 without the sheath.

In general, the preferred novel endoscopic device comprises a handle; means associated with the handle for detachably mounting a video camera therein; a rigid optic tube mounted to the handle and containing therein optical means for transmitting a focussing light reflected from a surface to be viewed onto the video camera; illuminating means for illuminating the surface to be viewed; video camera means detachably mounted to the handle; and a rigid, removable, sterilizable sheath over the rigid tube and illuminating means such that the tube, the optical system therein and the illuminating means are completely isolated from direct exposure to the surfaces to be viewed or surrounding surfaces.

The handle is preferably of a size and shape so as to allow the user to easily and comfortably hold and manipulate the device without touching the portion of the sheath which is inserted into the oral cavity to be viewed. Typically, the handle is formed from a plastic but may be made of other materials as well, e.g. wood, ceramic or metal.

The means for detachably mounting a solid state video camera into the handle can be any means known in the art. For example, the handle can be provided with a hollow bore having internal screw threads into which a camera can be screwed, or a simple tapered bore can be provided which mates with a tapered camera housing or a key and groove interconnection or a quick release snap-on interconnection can be provided.

The rigid optics tube is generally affixed to the handle opposite the camera. It may be permanently affixed to the handle or removably affixed thereto. If permanently affixed, the dimensions of the endoscopic portion of the device as well as the optical system contained within the tube are likewise fixed. Where the optics tube is removably affixed, so that an alternate tube can be placed on the handle, the length of the tube as well as the focal plane and magnification, if any, of the optical system can be changed.

The optics tube is preferably completely enclosed so that the optical system is protected thereby. Also, it is generally preferable, but not necessary, that the optics tube also contain therein the illumination means. The illumination means generally comprises a bundle of light transmitting fibers which transmits light from a light source, through the fiber bundle and out of the device so as to illuminate the area to be viewed. Typically, the optics tube is made of a rigid durable material such as stainless steel, but can be made of virtually any rigid material. When the tube is opaque, at least one transmitting window must be provided therein to allow light reflected from the surface to be viewed to be collected by the optical system for transmission onto the camera and when the optics tube also contains the illuminating means therein, a light transmitting window for the illuminating light must also be provided. This can be two separate windows or a single enlarged window. Any light transmitting material, e.g. glass or quartz, is suitable as a window material. Where the optical tube is itself transparent, a separate window is not required but the tube should be flat and polished in the area through which the light is transmitted so as not to distort the image. A feature of the novel invention is the use of a rigid, removable sheath which as indicated completely surrounds and isolates the optical tube, optical system and illuminating means. The sheath should itself be devoid of any optical components other than possibly one or more light transmitting windows aligned with the illuminating mean/and optical system to allow light to pass out of and into the device, respectively. The sheath should be made of a material which is sterilizable, i.e. autoclavable, e.g. stainless steel or other non-corrodible metal or alloy, a high temperature plastic or a ceramic. Preferably, the sheath fits coaxially over the optics tube, has a closed distal end and is secured to the handle in a manner to substantially prevent its rotation or movement during use.

This invention also contemplates and embodiment wherein a solid state video detector, e.g. a CCD chip is positioned so as to be directly illuminated with light reflected from the field to be viewed without the need for intermediate lens, prisms or the like.

A preferred embodiment of the novel device particularly useful as an intraoral endoscopic device is described with reference to the Figures.

Figure 4:
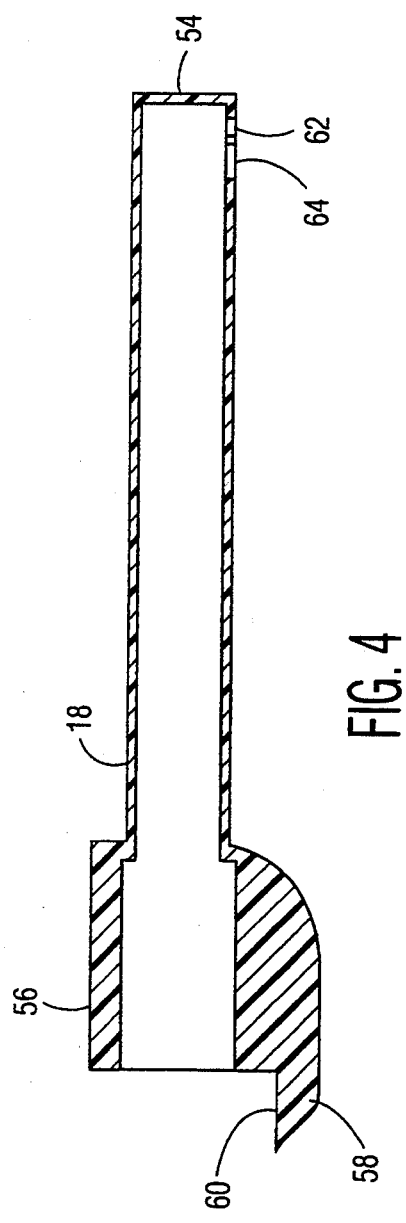
FIG. 4 is a side cross-sectional view of the sheath.

Referring to FIGS. 1-6, there is shown a novel device 1 comprising a hollow central support member 10 which acts as the handle for holding the assembled device 1 when in use; a narrow elongated lens tube 12 having an appropriate lens system 14 contained therein said tube 12 being mounted within and extending from the distal end 16 of the support member 10. A removable sheath 18, adapted to fit over and completely protect and isolate the lens tube 12 from exposure to the oral cavity to be viewed so as not to become contaminated therefrom, is positioned over the lens tube 12. Means are provided with respect to the support member 10 and the sheath 18 such that the sheath 18 will not be disengaged or move while the device 1 is in use. A solid state video camera 22 is removably mounted within the proximal end 24 of the support member 10. In addition, a fiber optic bundle 26 is provided. The fiber optic bundle 26 is coupled to a light source (not shown) at one end thereof and extends into and terminates within the narrow lens tube 12.

The support member or handle 10 is made in a shape and size which facilitates holding the device in operation without having to touch any portion of the device which may be inserted in the cavity to be viewed, e.g. the mouth. It may be made of any convenient rigid material including plastics and metals.

The distal end portion 16 of the handle 10 is cylindrical and is provided with a shallow groove 28 circumferentially the area around into which is placed an O-ring 30. A narrow lens tube hole 32 is centrally bored axially through the distal end portion 16 of the handle 10. This narrow lens tube hole 32 communicates with a centrally bored wide camera hole 34 which extends through a main body portion 36 of the handle 10. The distal part of the main body portion 36 of the handle 10 is provided with a flat surface 38. In addition, a fiber optic entrance hole 40 which communicates with the camera hole 34 is provided through the proximate end of the handle 10 below the camera hole 34.

The proximate end of the camera hole 34 is provided with means, such as a threaded portion 42, so as to removably accept the solid state video camera 22 therein.

The lens tube 12 is of a diameter such that it securely fits within the lens tube hole 32 of the handle 10. As can be seen from FIG. 3, the optical system 14 contained within the lens tube 12 comprises the fiber optic bundle 26 through which light from a light source (not shown) is transmitted through the lens tube 12 and emanates from the lens tube 12 via a lens tube transmissive window 44. Light reflected from the surface to be viewed is transmitted back into the lens tube 12 via an optical window 46 adjacent and proximate to the transmissive window 44. The reflected light entering optical window 46 adjacent and proximate to the transmissive window 44. The reflected light entering optical window 46 then passes through a series of optical imaging devices including a fight angle roof prism 48, a set of objective lenses 50, a rod lens 15 and a video relay lens 52. Inherent in the function of the roof prism is the reinversion of the image such that the image on the screen is not inverted with respect to the visual image of the oral cavity as seen by the dentist and movement of the device mimics the direction of movement on the screen. Absent the roof prism, the lens system inverts the image to give a mirror image. The final image is made to focus upon the solid state camera 22 which is mounted on the opposite end of the handle 10. The end 53 of the lens tube 12 is closed so as to prevent contamination of the optics. As can be seen with reference to FIGS. 5 and 6, the optical fibers 26 extend axially through lens tube 12 adjacent rod lens 15 until they approach the area of window 44 where the fibers are bent 90 degrees downwardly so as to terminate with their ends adjacent the window 44 in a direction essentially perpendicular to the axis of the lens tube 12. It will be understood that the invention is not limited to any specific lens system and any lens system which conveys the light to the video detector of the camera so as to give a sharp image which is not inverted is suitable. In fact, a lensless system wherein the video detector is directly illuminated also falls within the scope of the invention.

The sheath 18 is closed at its distal end 54 and when in operating position, concentrically surrounds lens tube 12. The proximal end 56 of the sheath 18 snugly fits over the distal end portion 16 of the handle 10. The O-ring 30 forms a seal so as to prevent contamination from entering the cavity formed by the space 57 (see FIG. 1) between the outside of the lens tube 12 and the inside of the sheath 18, thus preventing contamination of the lens tube 12 and obviating the need for sterilization of the lens tube 12. The proximal end portion 56 of the sheath 18 is provided with an extension 58 having a flat upper surface 60 which snugly mates with the flat surface 38 provided on the handle 10. This prevents rotation of the sheath 18 during use. The sheath is also provided with light transmitting glass or quartz windows 62 and 64 which are in registration with windows 44 and 46 of the lens tube so that light emanating from the lens tube 12 can pass out of the sheath 18, and the light reflected from the surface to be studied can pass through the sheath 18 into the optical lenses of the lens tube 12.

The embodiment shown in FIG. 7 is essentially the same as the previously described embodiment except that the lens system is replaced by a solid state video detector 66 positioned adjacent window 46 in tube 12 and means 68 are provided for transmitting the signal produced in the detector to the signal process or of the video camera. Also, the fiber optic illuminating means 26 is outside of, but adjacent the tube 12.

The novel device and system have several advantages over prior art devices. One primary advantage is an easily removable sheath which can be made of a rigid plastic material or of a metal such as stainless steel and which can be discarded (when made of and inexpensive plastic) or autoclaved or otherwise sterilized, separate and apart from the optical system, and which completely protects and isolates the tube containing the optical system from exposure to contamination.

A second advantage is the provision of a universal handle which negates the necessity of touching any part of the device which is inserted into the cavity to be viewed and also provides for quick and easy changing of video cameras according to the application. In addition, the lens tube could also be made interchangeable so that one can readily alter the lens system to fit ones need depending upon the application. Such interchangeability of camera and/or lenses greatly broadens the practical use of the device without substantial cost.

Still another advantage is that due to the preferred lens system, the width of the endoscopic portion of the device can be made relatively narrow e.g. $\frac{1}{4}$", so that it does not block the users field of view.

It should be understood that the embodiment shown and described herein is but one embodiment of the invention and it is not meant to be limiting but only exemplary. For example, while it is preferred that the handle be of a size large enough and shaped so that the user can easily hold and manipulate the device, the size and shape are not critical. Also, while engagement of the video camera to the handle is shown to be by means of a screw thread, virtually any means known for making readily disengageable connections, e.g. quick-disconnects, key and slot, snap-on, set screw, or other connections known in the art are suitable. Similarly the means for removably mounting the sheath over the lens tube and to the handle is not critical and may be altered in any manner which would accomplish sealing of the lens tube from the environment without rotation of the sheath. Also, where the sheath is a light transmitting plastic, the separate windows provided in the sheath can be eliminated. Further, while for use as an intraoral device the typical length of the lens tube and sheath is from 4 to 6 inches, these members can be made of virtually any length provided the optics can be made to accommodate the length either by different lens systems or transmission of a focused image to the camera such as by means of optical fibers.

What is claimed is:

1. An intraoral imaging device comprising a handle having communicating proximal and distal apertures therethrough, means associated with the proximal aperture for interchangeably mounting a video camera therein; a video camera having a video detector interchangeably mounted within said proximal aperture; a rigid optics tube mounted in the distal aperture of said handle and having an optical system therein for focussing light reflected from a surface to be viewed onto the video camera so as to create a non-reversed video picture, said optics tube further containing therein a fiber optic light source for illuminating the surface to be viewed; a rigid, removable, sterilizable sheath comprising a tubular distal portion which completely encloses, surrounds and protects the optics tube and its contents from exposure to the field to be viewed and contains no optical components of its own other than one or more windows for allowing illuminating light from the fiber optics to exit the sheath and reflected light to enter said optical system within said optics tube in a direction transverse to the axis of the optics tube, and a proximate portion which mates with a distal portion of said handle in a manner to prevent rotation of said sheath, said handle being of a size and shape configured to allow the user to continuously comfortably hold and manipulate the device without touching the tubular distal portion of the sheath.

2. A device for viewing a field within an oral cavity comprising a handle having a shape and size configured to allow for continuous and comfortable holding and manipulation of the device, while in use without touching any portion which is insertable into the oral cavity; a rigid optics tube extending from said handle and closed at its distal end; illuminating means for illuminating the field to be viewed; optical means for transmitting and focussing light reflected from the illuminated field to a video detector surface; a video camera including said video detector surface detachably mounted within said handle; a rigid, removable, sterilizable sheath secured to the handle and encasing said optics tube and said illuminating means so as to completely isolate them from contact with the oral cavity; and means for allowing light to pass from said illuminating means out of said sheath, and means for allowing light reflected from the field to pass through said sheath and optics tube into said optical means in a direction essentially transverse to the axis of the optics tube; and wherein said optical means includes means for providing an image that is not reversed with respect to the field as directly observed by the user.

3. The device recited in claim 2 wherein the means for providing a non-reversed image comprises a roof prism.

4. The device recited in claim 2 wherein said illuminating means is within said optics tube.

5. The device recited in claim 2 wherein said illuminating means is a fiber optic bundle.

6. The device recited in claim 2 wherein said illuminating means is external to said optics tube.

7. The device recited in claim 2 wherein the optics tube contains an optical system for conveying light reflected from the field and into the tube to a solid state video detector which detector is part of the video camera which is interchangeably mounted in the handle at the proximal end of said handle.

8. The device recited in claim 2 wherein the sheath is removably mounted on the handle in a manner such that the sheath cannot rotate.

9. The device recited in claim 8 wherein the optical means includes a roof prism, a rod lens at least one objective lens and a relay lens.

10. The device recited in claim 8 wherein the illuminating means comprises a fiber optic bundle contained within said optic tube.

11. The device recited in claim 8 wherein the sheath is comprised of a metal or metal alloy.

12. The device recited in claim 11 wherein said sheath is stainless steel.

* * * * *